United States Patent

Straten

Patent Number: 5,419,834
Date of Patent: May 30, 1995

[54] PRECIPITATING AGENT FOR THE PRECIPITATION OF HEAVY METALS

[76] Inventor: Gunter Straten, Grossheidstrabe 228, 52080 Aachen, Germany

[21] Appl. No.: 188,477

[22] Filed: Jan. 28, 1994

[30] Foreign Application Priority Data

Feb. 2, 1993 [DE] Germany .................. 43 02 910.8

[51] Int. Cl.$^6$ .................. B01D 21/01; B01D 47/06
[52] U.S. Cl. .................. 210/198.1; 55/228; 55/DIG. 25; 75/722; 95/234; 210/688; 210/725; 210/735; 210/914; 252/315.1; 423/210; 423/215.5; 502/516
[58] Field of Search ............. 95/133, 134, 234, 63–66; 96/52, 53; 55/228, DIG. 25; 210/673, 914, 688, 725, 728, 734, 735, 679, 198.1; 75/722; 423/210, 215.5, 228; 502/516; 252/315.01, 315.1, 8.551, 8.553; 166/292, 300, 294, 295

[56] References Cited

U.S. PATENT DOCUMENTS

| 3,617,570 | 11/1971 | Redmore | 210/735 |
|---|---|---|---|
| 3,755,161 | 8/1973 | Yokota et al. | 95/133 X |
| 3,783,158 | 1/1974 | Platzke et al. | 95/234 X |
| 3,873,581 | 3/1975 | Fitzpatrick et al. | 552/234 |
| 3,909,200 | 9/1975 | Redmore | 422/16 |
| 4,039,446 | 8/1977 | Ban et al. | 95/133 X |
| 4,044,098 | 8/1977 | Miller et al. | 95/234 X |
| 4,100,100 | 7/1978 | Clouse et al. | 423/228 X |
| 4,100,253 | 7/1978 | Dougherty | 423/87 |
| 4,102,804 | 7/1978 | Clouse et al. | 423/228 X |
| 4,142,875 | 3/1979 | Bohmholdt et al. | 95/234 X |
| 4,233,274 | 11/1980 | Allgulin | 95/234 X |
| 4,305,827 | 12/1981 | Sasaki | 210/688 |
| 4,431,563 | 2/1984 | Krawczyk et al. | 422/16 X |
| 4,446,056 | 5/1984 | Thompson | 252/391 |
| 4,465,593 | 8/1984 | Wemhoff | 210/96.1 |
| 4,479,879 | 10/1984 | Hashimoto et al. | 210/727 |
| 4,484,924 | 11/1984 | Pfleiderer et al. | 8/94.17 |
| 4,620,492 | 11/1986 | Vogg et al. | 95/234 X |
| 4,861,493 | 8/1989 | Jansen | 210/914 X |
| 5,145,012 | 9/1992 | Hutchins et al. | 166/292 |
| 5,246,594 | 9/1993 | Stegemann et al. | 210/743 |

FOREIGN PATENT DOCUMENTS

| 0043759 | 1/1982 | European Pat. Off. |
| 0333672 | 9/1989 | European Pat. Off. |
| 2628649 | 1/1977 | Germany. |
| 3907066 | 11/1991 | Germany. |

OTHER PUBLICATIONS

German Patent Cited By Applicant In Specification.

*Primary Examiner*—Richard L. Chiesa
*Attorney, Agent, or Firm*—Anthony J. Casella; Gerald E. Hespos

[57] ABSTRACT

A precipitating agent containing thioacetamide is described for the precipitating of heavy metals from flue gases and waste waters, it containing thioacetamide ($C_2H_5SN$) in a 1–20% aqueous solution, which, in addition, contains a buffer substance in order to prevent hydrolyric spontaneous decomposition, the solution having a pH of between 5.5 and 9.0.

18 Claims, 2 Drawing Sheets

PRECIPITATING AGENT FOR THE PRECIPITATION OF HEAVY METALS

BACKGROUND OF THE INVENTION

The present invention relates to a precipitating agent containing thioacetamide for the precipitation of heavy metals from flue gases or waste waters, a method for the production thereof, and the use thereof.

The precipitating agent serves, in particular, for the removing of heavy metals from flue gases and gas scrubbers of power plants employing fossil fuels and of garbage incineration plants. The agent serves furthermore for the precipitation of heavy metals from waste waters of combustion and garbage incineration plants as well as from other waste waters containing heavy metals.

From Federal Republic of Germany 39 07 066 C2 the use of thioacetamide for the decontaminating of sludge sediments is already known. Furthermore, a method of removing heavy-metal ions from aqueous solutions of complex compounds is already known from Federal Republic of Germany OS 26 28 649 in which salts of monothiocarbonic acids are used, possibly in the presence of a phosphate buffer.

From EP 0 043 759 A1, a hydrophilic substrate for the absorption of the metals is already known in which the precipitation of metal sulfides by an aqueous solution of sodium sulfite, potassium sulfite, ammonium sulfite or thioacetamide is also used.

Furthermore, from EP 0 333 672 A1 there is already known a slowly soluble solid product which is formed of substances which are capable or precipitating impurities in the waste waters of dental equipment. It is proposed, inter alia, that an organic compound, for instance thioacetamide, be used which produces hydrogen sulfide upon the hydrolysis.

In power plants which use fossil fuels and in garbage incineration plants which desulfurize and denitrogenize the flue gases in accordance with the wet scrubbing principle, a flue gas is produced which contains in part considerable concentrations of volatile heavy metals, for example arsenic (As), antimony (Sb), mercury (Hg), cadmium (Cd), lead (Pb), tin (Sn), zinc (Zn), and the like.

In particular, the presence of mercury in the flue gas results in great problems for various reasons. Another difficulty is represented by the presence of arsenic upon the firing of lignite, anthracite and heavy oil. Arsenic is contained, in part in considerable quantities, in many types of coal and in a few heavy oils and upon the burning of them necessarily it also enters into the flue gases, namely in gaseous state.

The desulfurization and denitrogenization of flue gases from the above-mentioned plants is effected traditionally in two fundamentally different ways, namely by a so-called dry scrubbing method and by a so-called wet scrubbing method.

The present invention serves, in particular, for use in the wet scrubbing of flue gases of garbage incineration plants and provides a special solution for the problems and goals in that field.

Combustion flue gases from power plants which burn fossil fuels as well as from garbage incineration plants contain, after passage through electrofilters and other fly-dust and particle separators, also gaseous components in addition to fractions of very fine particles. One central problem is represented in this connection by volatile heavy metals, particularly arsenic and mercury. Of the metals mentioned above, all, with the exception of arsenic and mercury, can be easily removed almost completely from the stream of gas merely by contact with water.

This is only imperfectly possible in the case of mercury and arsenic, which, on the one hand, causes measurable residual contents of these metals in the clean gas and, on the other hand, leads in the case of multi-step scrubbing methods, to an entrainment of these substances into the following stages. In multi-stage flue gas scrubbing plants, the first stage is generally operated as "acid scrubbing stage" with feeding of fresh water or else by recycling in order to retain the said heavy metals, hydrochloric acid and other impurities. The second stage operates either directly with milk of lime (emulsion of $Ca(OH)_2$ in water) or, more frequently, with caustic soda solution in order to remove sulfur dioxide from the flue gas. When sodium hydroxide is used, sodium sulfate ($Na_2SO_4$) is produced, which thereupon, in a "gypsum stage," is reacted with calcium chloride ($CaCl_2$) to form gypsum ($CaSO_4$) and sodium chloride (NaCl).

If arsenic or mercury enters into this $SO_2$-scrubbing stage, this necessarily leads to the undesired contaminating of the gypsum, which limits the use thereof or even makes it impossible. At the same time, measurable residual contents of the metals remain in the purified flue gas and thus enter the outer air.

The substantial elimination of arsenic in the flue gas from acid scrubbing stages of two-stage scrubbing systems can generally be effected without difficulty by the addition of suitable arsenic-combining substances. The removal of metals is considerably more problematic when arsenic and mercury or mercury alone are present as substantial impurities in the flue gas since the mercury is present in unstable transition stages of $Hg^I Hg^{II}$ as a result of the strongly reductive matrix (predominantly $SO_2$) in the hot acid scrubbing zone of the first scrubber. This Hg passes through the spray scrubbing in predominantly dissolved (more than 90%) but only as part of the total mass, into the aqueous acid phase, the gas being cooled to about 150° C. from its previous value of 180° C. to 230° C. Due to the strongly hydrochloric-acid pH (0.2–1.5), the $SO_2$ remains substantially dissolved in the flue gas.

In the case of acid scrubbing stages with water recycling, only a small partial stream per hour as removal of salts and sludge from the bottom of the scrubber is replaced by fresh water which leads to an enrichment of the dissolved mercury in the wash water. As a result of this, there is established within the gas-vapor-water phase a mercury equilibrium which is determined by the factors of Hg content of the raw gas, Hg content of the wash solution, temperature of the system, pressure of the system, pH, etc.

In accordance with the laws of physical chemistry, therefore, a substantial or even complete elimination of the mercury from the flue gas cannot be obtained by this method. A precipitation of the Hg as mercuric sulfide (HgS) fails as a result of the strongly reducing action of the hydrogen sulfide ($H_2S$) produced upon the use of polysulfide agents in acid solution, it effecting a partial disproportionation of the mercury into $Hg^{II}$ and $Hg^0$.

Upon the use of inorganic sulfide and polysulfide substances, there are obtained, depending upon the quantity of the precipitating agent used, between 5 and 30% of the mercury contained therein, as elementary mercury ($Hg^0$), which is entrained by the flue gas depending on the temperature in accordance with its partial pressure and thus carried along into the $SO_2$-scrubbing stage and there either passes into the gypsum or is brought, in part via the clean gas, back into the outer air.

The use of organic sulfur compounds is generally out of the question since, as a rule, they are only slightly, if at all, cohesive in acid solution and they form organic sulfur-mercury adducts which are split again thermally in the hot flue gas zone of the mercury. The limit values for mercury in the pure gas are at present 50 $\mu g/Nm^3$ Hg, which, however, can be maintained only with difficulty without precipitating agent. Furthermore, they are further reduced before long by the changing of the TA air so that a solution of the problem described becomes evermore urgently necessary.

The object therefore arises of providing a precipitating agent which under the action of heat, within the temperature range of 50° C. to 250° C., precipitates arsenic and mercury from flue gases and/or acid scrubber waste streams and with which the formation of hydrogen sulfide or other strongly reducing substances is suppressed. Another object of the present invention is to provide a method for the production of the precipitating agent and its use in a gas scrubbing solution system in which arsenic and mercury are precipitated either directly from the hot stream of gas or from the wash-solution stream of a temperature of 40° C. to 90° C. without resulting in the formation of elementary Hg. The precipitating agents and the methods of production and use are to be such that they can be used, in particular, for flue gas cleaning processes with two-stage scrubbing systems including a gypsum salt stage without any negative effects on the air, water or earth resulting upon their production or use due, for instance, to the liberation of dangerous reaction products.

SUMMARY OF THE INVENTION

The precipitating agent containing thioacetamide in accordance with the invention for the precipitating of heavy metals from flue gases or waste waters is characterized by the fact that it contains thioacetamide ($C_2H_5SN$) in a 1-20% aqueous solution which also contains a buffer substance in order to prevent hydrolytic spontaneous decomposition, the solution having a pH of between 5.5 and 9.0.

The precipitating agent of the invention is of good stability and remains stable for about 4 days without any measurable decomposition products. The precipitating agent, with the use of 1.5 kg per $m_3$ of scrubber waste water of a garbage incineration plant, is capable of precipitating up to 99.8% of the dissolved mercury contained therein and up to 72% of the arsenic contained therein without the formation of elementary mercury.

The chemical properties of thioacetamide are similar to those of acetamide, thioacetamide being mesomerism-stabilized, i.e., the C-N bond has a partial double-bond character, as a result of which the sulfur is bonding-activated.

With respect to inorganic acids, thioacetamide behaves as a weak base, salts with mesomerism-stabilized cations being formed with concentrated acids, they being easily hydrolytically split again.

By addition of a buffer substance, the hydrolytic spontaneous decomposition into $NH_3$, $H_2S$ and acetic acid can be prevented or slowed down and stabilization of the pH within the range of 5.5 to 9.0 obtained. Since the velocity of the hydrolyric spontaneous decomposition is increased with stronger concentrations of the aqueous solution, a 1-20% aqueous solution has been found to be stable for a particularly long period of time. The addition of the buffer substance, in particular at a temperature of between 50° C. and 250° C., favors the splitting-off of thiosulfur for the combining with heavy metals. The buffer substance therefore, particularly in dilute aqueous thioacetamide solutions, leads to the effective precipitation of arsenic and mercury from hot acid flue gases in hot scrubbing solution waste streams of gas scrubbing plants, the thioacetamide being stabilized in the aqueous phase against decomposition and in this way having a longer stability and possibility of storage, for instance in tanks. Furthermore, assurance is had that, upon the reaction of the precipitating agent, no $H_2S$ will be liberated in the acid scrubbing zone.

The thioacetamide is preferably used in a 1-10% aqueous solution, and in particular a 4-6% aqueous solution, and, even more particularly, in an approximately 5% aqueous solution. With these concentrations by weight, the decomposition time of the thioacetamide is short with still acceptable effectiveness.

As buffer substance, a phosphate is suitable, it however being required in large amounts.

As an alternative, or in addition, the buffer substance contains a carbonate, which is obtainable at low cost on the market.

Finally, the buffer substance, as alternative or in addition, can contain a borate, which also has good buffering properties.

As buffer substance, there is preferred, in particular, a bicarbonate, which has particularly good buffering properties. As bicarbonate, sodium bicarbonate is preferably used.

The buffer substance is preferably employed in a concentration of 1-20% by weight, more preferably 2-10% by weight, and with particular preference 3-5% by weight.

The adjustment of pH plays a considerable role in connection with the decomposition of thioacetamide since the latter decomposes both in acid solution (pH 0.5-3.5) and in alkaline solution (pH 10-13.5) rapidly with the formation of ammonia, hydrogen sulfide and acetic acid. As a practical matter, the setting of the pH at 7.0 to 8.5, and in particular at 8.1 to 8.2, is particularly preferred since, as will be shown below, particularly long periods of stability are obtained within this range. The maximum is at about pH 8.2.

In a preferred embodiment, the precipitating agent of the invention can be used not only for the precipitation of arsenic and mercury from flue gases and scrubber waste streams, but also for the precipitating of heavy metals from waste waters within the entire pH range of 0 to 14. Sodium hydroxide or caustic soda solution is added, preferably in a concentration by weight of 2-8%, and more particularly 3-7% and especially 4-6%. Thioacetamide decomposes completely under the action of caustic soda in dilute aqueous solution within 24 hours, forming ammonia, sodium hydrosulfide and sodium acetate, whereby heavy metals are precipitated with high efficiency throughout the entire pH range.

As an alternative for or in addition to sodium hydroxide, sodium sulfite can be added, preferably within a weight ratio of 0.5–1.5%, more preferably 0.8–1.2% and with particular preference 0.91.1 wt. %.

As an alternative or in addition, the precipitating agent can contain sodium dithionite in a weight ratio of 2.5–7.5%, preferably 3.5–6.5% by weight, and particularly 4.5–5.5% by weight. The reactivity of this mixture is based, on the one hand, on the action of the dithionite and, on the other hand, on the action of the decomposition products of the thioacetamide.

The method of the invention for the production of the precipitating agent includes the production of an aqueous solution of the buffer substance, the pH of which is controlled and possibly adjusted with HCl or NaOH. Thereupon, the thioacetamide is added in the proper amount. The addition of the buffer substance before the thioacetamide has been stirred-in is important in order to avoid higher hydrogen ion concentrations already upon the dissolving.

Upon the addition of thioacetamide, the temperature is preferably maintained between 15° C. and 20° C. Higher temperatures are disadvantageous.

The method of the invention for the production of a precipitating agent for, preferably, the treatment of waste water includes the dissolving of sodium hydroxide in water, whereupon sodium sulfite and/or sodium dithionite are possibly added and finally thioacetamide.

The use of the precipitating agent of the invention for the purification of the flue gas of a combustion plant which has a wet-scrubbing apparatus is characterized by the fact that the precipitating agent is added to a wash-water feed which is fed to the wet-scrubbing apparatus. As an alternative, or in addition to this, the precipitating agent is added to a wash-water discharge coming from the wet-scrubbing apparatus. Since the discharge is returned in certain wet-scrubbing devices to the feed, the precipitating agent passes in all cases into the spray region.

In the feed there is preferably provided a mixing device which serves to mix the precipitating agent with the wash water. It is also preferred that the precipitating agent be adjusted to a percentage of mercury contained in the inlet or outlet of a molar ratio of 8–12:1 and preferably 9–11:1 and very particularly to about 10:1. The ratio of 10:1 represents at the same time the limit concentration at which still only a very small amount of elementary mercury is produced. This molar ratio should therefore not be substantially exceeded upon use.

BRIEF DESCRIPTION OF THE DRAWINGS

Further advantages, features and possible uses of the present invention will become evident from the following description of embodiments, read in conjunction with the drawing, in which.

DETAILED DESCRIPTION OF THE PREFERRED EMBODIMENT

Figure 1:
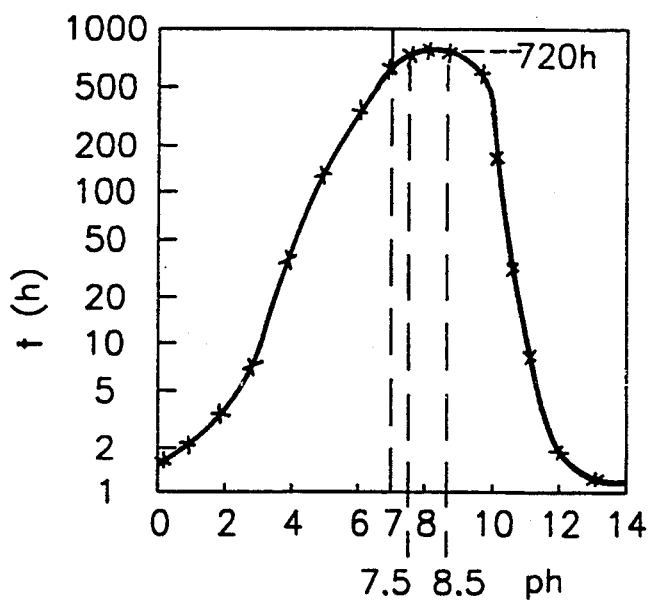
FIG. 1 shows the results of an investigation as a function of the pH.

The graph shown in FIG. 1 is based on a 5% aqueous solution of thioacetamide produced on a large industrial scale for the tests. As measurement parameters, the decomposition products ammonia ($NH_3$), hydrogen sulfide ($H_2S$), and acetic acid ($CH_3COOH$) have been selected. Different buffer mixtures were used for adjusting the pH in each case.

The examination results given in FIG. 1 show that an aqueous solution of thioacetamide is preferably stabilized against decomposition in the pH range of between 7.5 and 8.5 and remains stable upon storage for at least 720 hours (30 days). The time t shown in the figure is the time until the decomposition of 1% of the thioacetamide present (originally 50 g/L $\approx$ 5 wt. %), the temperature T during the storage time being 20° C.

Figure 2:
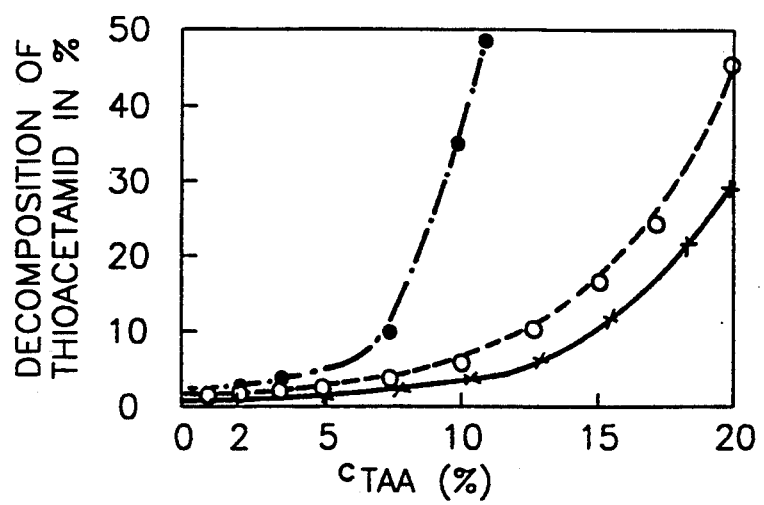
FIG. 2 shows the spontaneous decomposition of thioacetamide as a function of the concentration of the solution at different values of pH.

The graph in FIG. 2 of the spontaneous decomposition of thioacetamide as a function of the concentration of the solution at different values of pH is based on a time t of 240 hours at a temperature T of 20° C. The individual curves refer to a pH of 8.2 (solid line), a pH of 5.2 (dashed line), and a pH of 1.0 (dash-dot line). It can be noted from FIG. 2 that with 5 wt. % thioacetamide, the most favorable concentration of the active substance is present. Depending on the pH, the decomposition increases greatly at higher concentrations.

Figure 3:
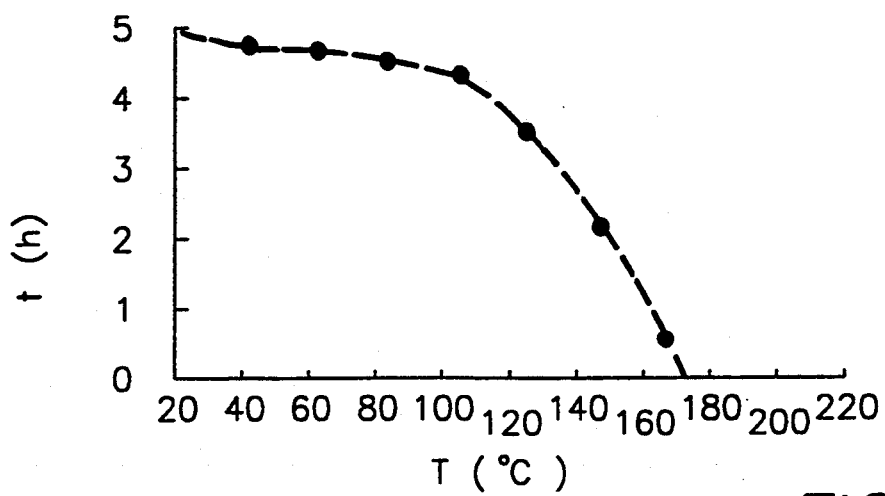
FIG. 3 shows the variation with time of the spontaneous decomposition of a 5% aqueous thioacetamide solution as a function of the temperature.

FIG. 3 shows the variation with the time of the spontaneous decomposition of the 5% aqueous thioacetamide solution as a function of the temperature, a concentration of thioacetamide of 5 wt. % and a pH of 1.0 being taken as basis. The time is clocked upon decomposition of 5% of the thioacetamide present, it being found that up to about 100° C. there is still a stability of up to about 4 hours, and above 100° C. a stability which drops linearly with the temperature to about 0.5 hours at 160° C.

The results of FIGS. 2 and 3 show that the amount of substance necessary for the binding of the metals should be dosaged as precisely as possible and must in no case be overdosed by more than 5 times the quantity since, in such case, hydrogen sulfide is liberated from the decomposition of the unconsumed thioacetamide, which can cause a reduction of the mercury to elementary mercury.

FIG. 3 furthermore shows the problem of contact of the thioacetamide directly in the spray zone of the flue gas scrubbing at 150° C. since the spontaneous decomposition commences very rapidly at this temperature. Since the contact time in this zone is, however, short, the optimum between speed of binding, efficiency, and minimum spontaneous decomposition of the unconsumed excess of thioacetamide must be determined by a large-scale technical experiment.

EXAMPLE 1

There is described below and example of the production of a ton of a 5% aqueous solution of thioacetamide containing 4% by weight of sodium bicarbonate.

A container of GFK, PP or special steel is used, the agitator consisting of special steel with a plurality of paddles which can be adjusted to speeds of 30 to 180 rpm.

Technically pure 99% thioacetamide leaflets and technically pure sodium bicarbonate of a purity of >99% in powder form, as well as desalinated water or drinking water of a total hardness of <5° German hardness are used.

40 kg of sodium bicarbonate are first of all added to 910 liters of water and completely dissolved. The pH is then checked and, if necessary, brought to precisely 8.3 by means of HCl or NaOH. 50 kg of thioacetamide are then introduced into the buffered solution, the temperature being maintained between 15° C. and 20° C. After the thioacetamide has completely dissolved—about 2 hours—the pH is checked and brought to 8.2.

Figure 4:
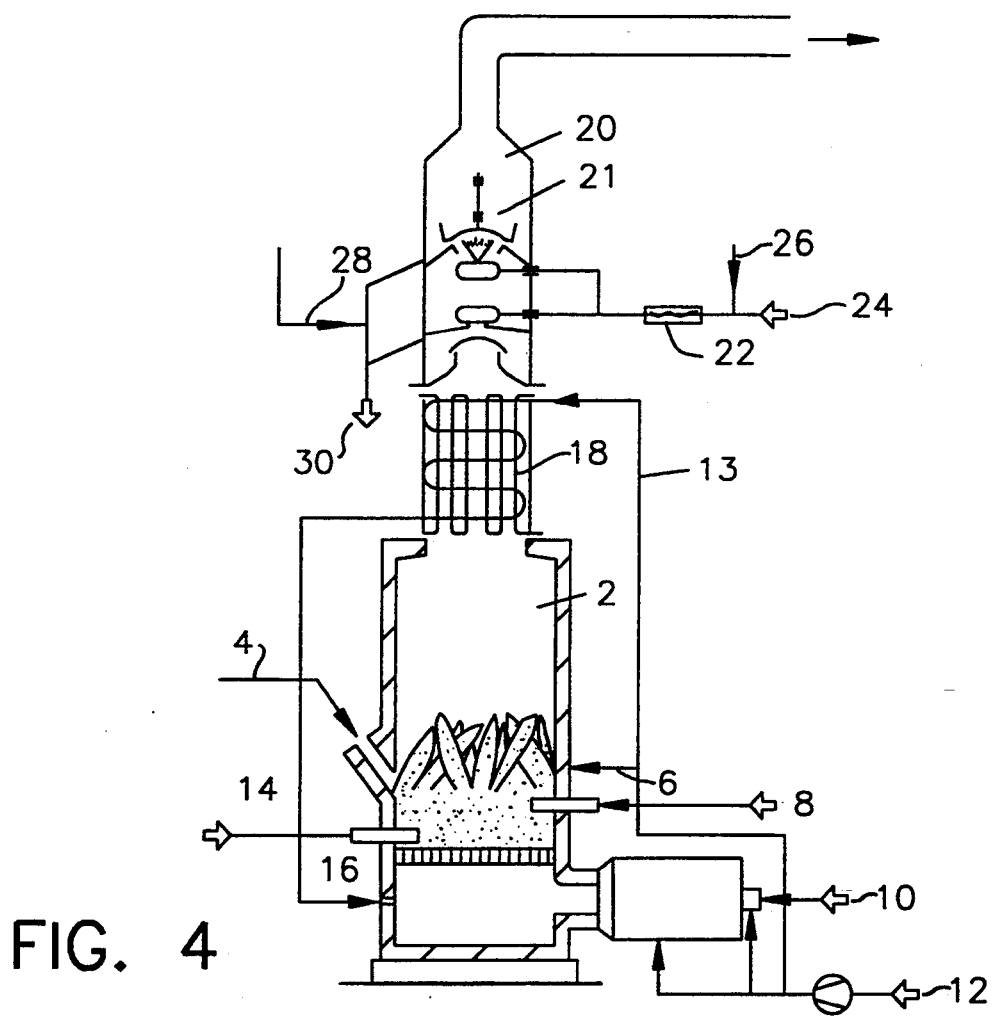
FIG. 4 shows an apparatus for introducing thioacetamide into the first scrubbing stage of a fluidized-bed reactor.

FIG. 4 shows an apparatus for the feeding or use of the precipitating agent in the process of the wet purification of combustion plants which operate in accordance with the wet-scrubbing principle.

The apparatus has a burner 2, into which a burner channel 10 and an air-introduction channel 12 are introduced. Furthermore, a waste substance to be burned is introduced into the burner through a channel 8 and a supplementary fuel is introduced through a channel 14. From the air channel 12, there branches off a channel 13 which is conducted to a heat exchanger 18 which heats the air and conducts it through an inlet 16 into the burner. Secondary air is introduced through an inlet 6.

Above the heat exchanger 18 there is an acid scrubbing stage 20 which has several spray devices 21. The spray devices 21 are connected to a static mixer 22 which, in its turn, is connected to a wash-water feed line 24. A feed line 26 for the precipitating agent of the invention debouches into the wash-water feed line 24.

From the collectors of the spray devices 21, there extend wash-water discharge lines which collect in a line 30 the wash water to be disposed of. A second feed line 28 for thioacetamide precipitating agent, which is added only in the wash water outlet, debouches into the wash-water discharge line 30.

The precipitating agent of the invention can be added in concentrated form, but preferably in dilute form, to the wash water in the acid-scrubbing stage 20, so that it passes, together with the wash water, into the spray device 21. An addition of the precipitating agent into the wash-water discharge stream which has a temperature of 50° to 80° C. is also possible. The feed lines 26 and 28 are used alternately or in combination, depending on the technical conditions of the plant. The design is to be determined in an industrial large-scale test.

If the precipitating agent of the invention is sprayed through the feed line 26 into the feed, it is mixed in a static mixer 22. If the precipitating agent is added into the wash water discharge, this can be done in concentrated or dilute form. The two methods differ therein that there is a temperature difference of about 100° C. between the gas-spray zone and the discharging stream of spray water. In the region of the spray zone the temperatures are between 180° C. and 230° C. and in the discharge stream between 50° C. and 90° C.

Figure 5:
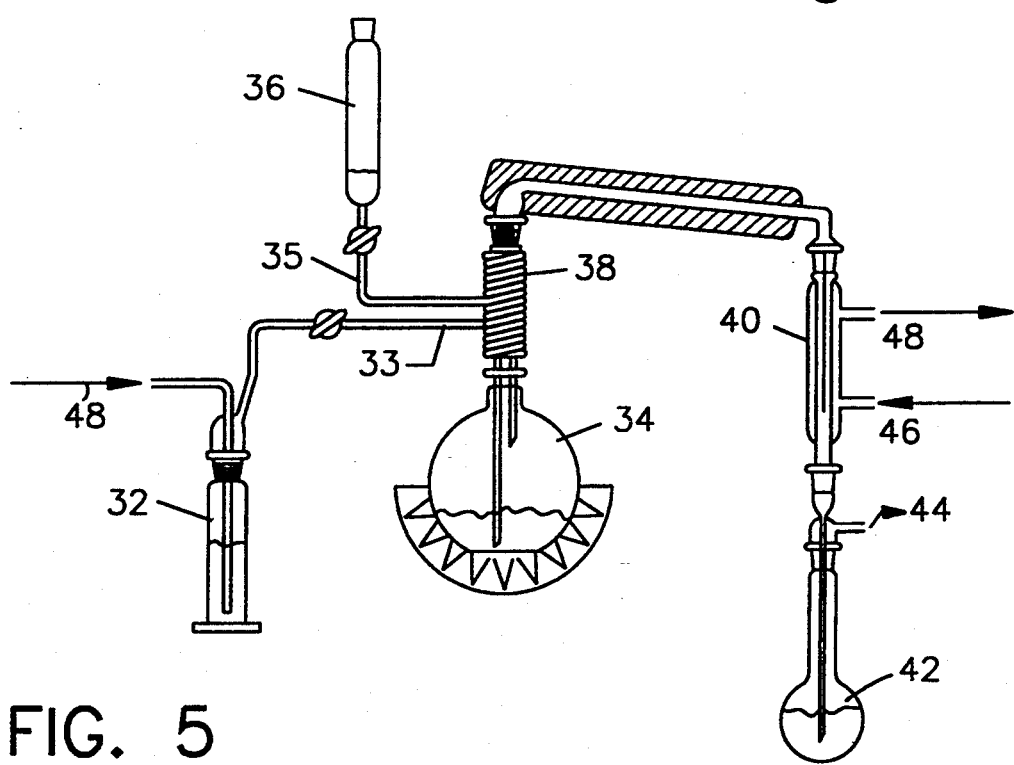
FIG. 5 shows a measurement apparatus for determining the mercury balance after a precipitation in scrubbing discharge of a temperature of 100° C.

The efficiency of the thioacetamide precipitating agent of the invention was tested in a laboratory experiment with an apparatus shown in FIG. 5.

The apparatus shown in FIG. 5 has a wash bottle 32 which serves to receive $KMnO_4$ wash solution for $N_2$, into which a tube 48 extends for the introduction of $N_2$. From the wash bottle 32, a line 33 leads to a distillation flask 34 which contains 100 mL of acid scrubber discharge-stream solution and is provided with a heating device. From an upper region of the flask 34, a tube 35 with dosaging cock, leads to a container 36 containing thioacetamide precipitating agent. A distillation bridge 38, which serves to receive the distillate, is provided with heat insulation as is a transfer tube which is connected with a distillation condenser 40. The heat insulation of the bridge 38 and of the transfer tube consists of glass wool with aluminum. The distillation condenser 40 is connected with an input connection 46 and an output connection 48 for the passage of the water circuit which serves for the cooling. Finally, the line is conducted into a collecting container 42 for elementary mercury, which is filled with 50 ml of aqua regia. A nipple 44 for the removal of $N_2$ extends from the upper region of the latter, there branches off. The $N_2$ thus drives from the inlet 48 to the outlet 44 and forces the distillate into the container 42.

As preparation for the test, 100 mL of the acid discharge water is introduced into the reaction flask 34. As source of heat, a heating mushroom jacket is used which covers the lower region of the reaction flask. The amount of the 5% precipitating agent solution provided in each case is introduced into the container 36 which serves a precipitating agent storage. Into the collecting receiver 42, which serves as distillation receiver, there are introduced 50 ml of aqua regia in order to collect any $Hg^0$ which has been produced and can be expelled. The apparatus is closed, the precipitating agent is admitted from the container 36 into the reaction flask 34 and thereupon 1.5 liters/minute of $N_2$ are flushed through the measurement system.

The nitrogen is purified with acid $KMnO_4$ solution in the wash bottle 32 before being introduced into the distillation flask 34. The reaction flask 34 is heated to boiling and 30 ml are distilled in the course of 45 minutes into the receiving container 42 for aqua regia. Thereupon, the rest of the reaction flask is transferred into a 100 mL graduated cylinder and, after cooling to precisely 20° C., filled with water, whereupon a part is sharply filtered through a membrane filter (0.5 $\mu$m).

The residue and the filtrate are digested and the total amount of Hg as well as the dissolved amount of Hg determined. The distillate is also made up to 100 mL with water and the elementary portion of the mercury ($Hg^0$) contained therein is determined. With this arrangement, the determination of the total balance of the mercury is possible.

In Tests 1 to 3 described below, the acid discharge water of the first stage from a garbage incineration plant is distilled without addition (Test 1), with a conventional polysulfide (Test 2) and with a 5% thioacetamide solution (Test 3). The waste water had the following characteristic data:

Total Hg : 6740 $\mu$g/L
Dissolved Hg: : 5330 $\mu$g/L
Elementary Hg : 11 $\mu$g/L
pH : 1.4

In Tests 5 to 8, a more highly laden waste water from the same plant was examined, it furthermore containing 184 mg/L of lead (Pb). The water had the following data:

Total Hg : 19500 $\mu$g/L
Dissolved Hg: : 19200 $\mu$g/L
Elementary Hg : 8.5 $\mu$g/L
Total Pb : 184 mg/L
Dissolved Pb: : 183 mg/L
pH : 0.5

The results of the tests are listed below:

TEST 1

In the first test, 100 ml of scrubber waste water were heated in the reaction flask without any addition to 100°

C. and gasified with 1.5 L/min of $N_2$ during a 45 minute distillation.

Thereupon, the following Hg contents were measured after the treatment described below:
Distillation residue:
Total Hg : 6730 μm/L
Dissolved Hg : 5690 μg/L
Distillate:
Elementary Hg : 13.4 μg/L

TEST 2

In the second test, 0.15 g, corresponding to 1.5 kg/m³ of a polysulfide precipitating agent was added to the 100 ml of waste water in the reaction flask and then treated as in Test 1. The following Hg contents were measured:
Distillation residue:
Total Hg : 6030 μm/L
Dissolved Hg : 3405 μg/L
Distillate:
Elementary Hg : 710 μg/L

TEST 3

In the third test, 0.10 g, corresponding to 1.0 kg/m³ of a 5% thioacetamide solution in accordance with the invention was added to the 100 mL of waste water in the reaction flask and then treated as in Test 1. The following Hg contents were measured:
Distillation residue:
Total Hg : 6735 μm/L
Dissolved Hg : 240 μg/L
Distillate:
Elementary Hg : <1 μg/L

TESTS 5 to 8

In the Tests 5 to 8, a waste water of higher mercury content from a garbage incineration plant was used. Furthermore, this waste water contained a considerably amount of lead. By the tests, an optimal dosage was to be determined and, in addition, it was to be checked whether portions of lead, in particular are also, in part, precipitated at the low pH of 0.5.

The waste water had the following initial data:
Total Hg : 19500 μg/L
Dissolved Hg: : 19200 μg/L
Elementary Hg : 8.5 μg/L
Total Pb : 184 mg/L
Dissolved Pb: : 183 mg/L
pH : 0.5

The tests were carried out in a manner similar to Tests 1 to 3. Only the amount of the 5% thioacetamide solution added was varied. The following results were obtained:

| Test No. | Amt. TTA 5% added (kg/m³) | Distillation Residue Tot. Hg (μg/l) | Distillation Residue Diss. Hg (μg/l) | Distillate Hg⁰ (μg/l) | Distillation Residue Tot. Pb (mg/l) | Distillation Residue Diss. Pb (mg/l) |
|---|---|---|---|---|---|---|
| 5 | 0.5 | 19500 | 14500 | >1 | 184 | 183 |
| 6 | 1.0 | 19500 | 8600 | >1 | 184 | 184 |
| 7 | 1.5 | 19500 | 471 | 1 | 184 | 183 |
| 8 | 2.0 | 19500 | 120 | 1.8 | 184 | 183 |

TEST 9

The waste water used for Test 9 contained scarcely any arsenic (<10 μg/L). Therefore, 5 ml of a concentrated stock solution (1 g/L $As^{3+}$) was added to 1 liter of the waste water from Tests 5 to 8. The waste water then had the following concentrations.
Total Hg : 19480 μg/L
Dissolved Hg: : 19185 μg/L
Elementary Hg : 8.4 μg/L
Total As : 4980 μg/L
Dissolved As: : 4950 μg/L Thereupon, the waste water was treated in accordance with the test setup described with the addition of 1.5 kg/m³ of 5% thioacetamide solution and then examined.

The following results were obtained:
Total Hg : 19480 μg/L
Dissolved Hg: : 560 μg/L
Elementary Hg : 1 μg/L
Total As : 4980 μg/L
Dissolved As: : 1390 μg/L

Experimental Results a) Tests 1 to 3

The blind test without addition of precipitating agents shows that 21.0% of the mercury present is present undissolved and 78.84% ionically dissolved. Only 11 μg/L corresponding to 0.16% are present in elementary form as $Hg^0$. After the action of heat (Test 1) without additions of precipitating agent, the result changes without basic shifts to the $Hg^0$. The content of total Hg with 6730 μg/L remains approximately the same, but 5690 μg/L corresponding to 84.5% thereof is ionically dissolved. The percentage of elementary Hg increases slightly to 13.4 μg/L, corresponding to 0.2%. The result of the test with a polysulfide precipitating agent (Test 2) shows a fundamental change in the conditions. The residual content of mercury in the distillation residue is decreased to 6030 μg/L corresponding to 89.5%. Referred to the initial concentration, 50.4% hereof is ionically dissolved and 10.5% present in elementary form as $Hg^0$ which is found again This result coincides substantially with a large-scale technical experiment in the garbage incineration plant from which the waste water comes. The result at the same time confirms the closeness to reality of the laboratory test setup. The result of Test 3 with the 5% thioacetamide solution shows practically complete retention of the mercury (6735 μg/L), of which only 240 μg/L corresponding to 3.56% is still present dissolved. The proportion of elementary mercury is 1 μg/L in the distillate.

b) Tests 5 to 9

The results of Tests 5 to 9 confirm in principle the results of Test 3. The use of 1.5 kg/m³ of a 5% thioacetamide solution shows, with 97.6% precipitation (Test 7) a reasonable result. The 1 μg/L of elementary mercury found in the distillate, however indicates that the optimal molar ratio of thioacetamide to mercury (TAA:Hg) of 10:1 found for practical use represents at the same time the limit concentration at which only very little $Hg^0$ is still produced. This molar ratio of use should therefore not be substantially exceeded.

The result of Test 9 shows, in addition to the constant concentration of lead, independently of the dosage practically equally good precipitation of Hg (97.1%) in the same way as Test 7. In addition, 72.1% of the arsenic added as standard was also precipitated. Neutralization tests then carried out showed that already as from a pH of 2.8, other heavy metals are precipitated by the remaining excesses of the thermally split thioacetamide. As a result of this, no excess precipitating agent can be removed from the waste-water neutralization present after the acid scrubbing.

An ecotoxicological consideration of the addition of thioacetamide in the flue gas and in the acid scrubber discharge streams of gas purification plants is given below.

A dose of 1.5 kg/m³ of a 5% thioacetamide solution corresponds to an amount of substance used of $$1500 \times 0.05 = 75 \text{ g/m}^3$$

This amount of substance, which is practically precisely 1 Mol of the substance per cubic meter of waste water does not, in the case of total consumption of the sulfur, produce any free residual amounts of thioacetamide which could pass via the neutralization plant into the ground water or a municipal waste-water purification plant.

Upon the consumption of the substance, acetic acid or acetate and ammonia-nitrogen are theoretically liberated as secondary products, the two of which contain only very small toxic potentials from an ecotoxicological standpoint.

In the example set forth, there is produced a maximum of 60 mg/L acetate and 14 mg/L ammonia-nitrogen, which at the same time represent the upper limit, since, as a rule, the amount of mercury in waste waters of garbage incineration plants and power plants is generally only within the region of about 5 mg/L.

Laboratory examination confirm that only the aforementioned secondary products acetic acid/acetate and ammonia-nitrogen ($NH_3$-N) are formed and that no free thioacetamide exits from a subsequent neutralization stage. To be sure, the measurements also showed that, of the theoretically calculated amount of 60 mg/L acetic acid or its salts, only 8 mg/L can be measured in the clear water phase after a milk-of-line neutralization. Of the remaining 52 mg/L, 48 mg/L were found again after distillation of the lime-gypsum sludge of the neutralization, so that there is confirmation that an approximate balance is present. Only 2.2 mg/L of the $NH_3$-N concentrations which could be theoretically released were found in the clear water after the neutralization.

Since the neutralization takes place only up to a pH of 8.5, no gaseous losses of $NH_3$ can be explained. The assumption that a part of the $NH_2$ group which is thermally split off reacted with $NO_x$ compounds in the flue gas so as to form $N_2$ is however explainable. As relevant resulting contents from the use of thioacetamide for the purification of flue gases, therefore a maximum of 9 mg/L CSB and 2.2 mg/L $NH_3$-N are to be expected at the outlet of a neutralization plant.

EXAMPLE 2

In the following, there will be described the production of a precipitating agent for the precipitating of heavy metals from waste waters of combustion plants and garbage incineration plants as well as from other waste waters containing heavy metals.

The precipitating agent described above for the precipitation in particular of arsenic and mercury from flue gases and scrubber discharge streams changes its properties if further addition substances, in particular caustic alkali, here preferably caustic soda (NaOH), are added. A precipitating agent which precipitates heavy metals in the entire pH range of pH 0 to 14 of the recipient (waste water, etc.) is described below. This precipitating agent, however, is not suitable for flue gases.

Composition of the precipitating agent of the invention:

50 kg sodium peroxide, beads, solid
10 kg sodium sulfite
50 kg sodium dithionite
50 kg thioacetamide
840 L demineralized water For the production of the precipitating agent of the invention, there are added to 840 L of demineralized water, in succession, 50 kg of NaOH beads, and after the dissolving thereof, 10 kg of sodium sulfite, and after the dissolving of it 50 kg of sodium dithionite, and finally 50 kg of thioacetamide. After the complete dissolving of all components (about 3 hours) the solution is allowed to react for a further 24 hours. At the end of this time, the solution has a clear odor of ammonia, whereby the necessary complete reaction is indicated. The reactivity of the mixture is based, on the one hand, on the action of the dithionite combined with the decomposition products of the thioacetamide. Thioacetamide decomposes completely under the action of caustic soda in dilute aqueous solution within 24 hours into ammonia, sodium hydrosulfide and sodium acetate. As a result of this, the reaction mixture is formed which is suitable for precipitating heavy metals from waste waters between a pH and 0 and 14 with great effectiveness.

I claim:

1. A precipitating agent for precipitating heavy metals from flue gases and waste waters, said precipitating agent comprising thioacetamide ($C_2H_5SN$) in a 1–20% aqueous solution and a buffer substance in said aqueous solution to prevent hydrolytic spontaneous decomposition, the solution having a pH of between 5.5 and 9.0.

2. A precipitating agent according to claim 1, wherein the thioacetamide is present in a 1–10% aqueous solution.

3. A precipitating agent according to claim 1, wherein the buffer substance contains a phosphate.

4. A precipitating agent according to claim 1, wherein the buffer substance contains a carbonate.

5. A precipitating agent according to claim 1, wherein the buffer substance contains a borate.

6. A precipitating agent according to claim 4, wherein the buffer substance contains a bicarbonate.

7. A precipitating agent according to claim 6, wherein the buffer substance contains sodium bicarbonate ($NaHCO_3$).

8. A precipitating agent according to claim 1, wherein the buffer substance is present in the solution in a concentration of 1–20% by weight.

9. A precipitating agent according to claim 1, wherein the solution has a pH of 7.0–8.5.

10. A precipitating agent according to claim 1, for the treatment of waste water, comprising sodium hydroxide (NaOH).

11. A precipitating agent according to claim 10, comprising sodium hydroxide in a concentration of 2–8% by weight.

12. A precipitating agent according to claim 10, wherein the sodium hydroxide is dissolved in water, that thereupon the buffer substance is added, and that finally the thioacetamide is added.

13. A precipitating agent according to claim 1, comprising sodium sulfite.

14. A precipitating agent according to claim 13, comprising sodium sulfite in a ratio by weight of 0.5–1.5 wt. %.

15. A precipitating agent according to claim 1, comprising sodium dithionite.

16. A precipitating agent according to claim 15, comprising sodium dithionite in a ratio by weight of 2.5–7.5 wt. %.

17. A precipitating agent according to claim 1, produced by the method of preparing the aqueous solution of the buffer substance, adjusting the pH of the solution, and adding the thioacetamide.

18. A precipitating agent according to claim 17, wherein the temperature upon the addition of the thioacetamide is maintained between 15° C. and 20° C.

* * * * *